United States Patent
Yoshinaga et al.

[11] Patent Number: 5,879,837
[45] Date of Patent: Mar. 9, 1999

[54] STYRYLCOUMARIN COMPOUND, PHOTOSENSITIVE RESIN COMPOSITION, AND HOLOGRAM RECORDING MEDIUM

[75] Inventors: Yoko Yoshinaga, Kawasaki; Susumu Matsumura, Kawaguchi; Naosato Taniguchi, Machida; Shin Kobayashi, Atsugi; Toshiyuki Sudo, Kawasaki; Hideki Morishima, Tokyo; Tadashi Kaneko, Isehara, all of Japan

[73] Assignee: Canon Kabushiki Kaisha, Tokyo, Japan

[21] Appl. No.: 961,136

[22] Filed: Oct. 30, 1997

Related U.S. Application Data

[63] Continuation of Ser. No. 625,303, Apr. 1, 1996, abandoned, Continuation of Ser. No. 237,105, May 3, 1994, abandoned.

[30] Foreign Application Priority Data

May 11, 1993 [JP] Japan ................................. 5-132482

[51] Int. Cl.$^6$ ......................................................... G03H 1/04
[52] U.S. Cl. ........................... 430/2; 430/1; 430/281.1; 430/285.1; 430/286.1; 359/3; 522/8; 522/13; 522/15; 522/16; 522/34
[58] Field of Search .................. 359/1, 3; 430/1, 430/2, 290, 281.1, 285.1, 286.1, 945; 522/8, 13–16, 23, 34

[56] References Cited

U.S. PATENT DOCUMENTS

| | | | |
|---|---|---|---|
| 3,380,831 | 4/1968 | Cohen et al. | 96/115 |
| 4,147,552 | 4/1979 | Specht et al. | 522/34 |
| 4,289,844 | 9/1981 | Specht et al. | 522/34 |
| 4,505,793 | 3/1985 | Tamoto et al. | 522/34 |
| 4,921,827 | 5/1990 | Ali et al. | 522/34 |
| 5,055,372 | 10/1991 | Shanklin et al. | 430/138 |
| 5,102,775 | 4/1992 | Okuhara et al. | 522/15 |

FOREIGN PATENT DOCUMENTS

| | | |
|---|---|---|
| 0022188 | 1/1981 | European Pat. Off. . |
| 0523715 | 1/1993 | European Pat. Off. ............... 430/2 |
| 0538997 | 4/1993 | European Pat. Off. . |
| 1-259702 | 11/1990 | Japan . |

OTHER PUBLICATIONS

Shoemaker et al., "Experiments in Physical Chemistry" (©1981) pp. 412–414.

F.M. Hamer, "The cyanine Dye and Related Compounds" (©1964) pp. 688–690.

O. Svelto, "Principles of Lasers" Third Ed. (©1989) pp. 331–333.

Chem. Abstracts, vol. 114, No. 18, 1991 Ab. No. 165100t, p.19, based on JPA–02–279,702.

Williams, et al, "Ketocoumarins as Photosensitizers and Photoinitiators", Polym. Eng. & Sci., vol. 23, No. 18, Dec. 1983, pp. 1022–1024.

Specht, et al, "Ketocoumarins", Tetrahedron, vol. 38, No. 9, pp. 1203–1211, 1982.

Crivello, et al "Aromatic Bisvinyl Ethers:—" J. Polym. Sci., Polym. Chem. Ed., vol. 21, pp. 1785–1799, 1983.

F.M. Hamet "The Cyanie dyes and Related Compounds" ©1964 pp. 688–690.

Shoemaker et al. "Experimetns in physical Chemistry" ©1981 pp. 412–414.

*Primary Examiner*—Martin Angebranndt
*Attorney, Agent, or Firm*—Fitzpatrick, Cella, Harper & Scinto

[57] ABSTRACT

A styrylcoumarin compound jointing a styryl group by—(C=C)n—portion and having —$NR_1R_2$ group, wherein n is an integer of 2 to 4, and each R is a proton or an alkyl group having 1 to 10 carbon atoms. A photopolymerizable composition comprises the styrylcoumarin compound as a photosensitizer, a polymerization initiator and a polymerizable compound. A photocrosslinking composition comprises the styrylcoumarin compound as a photosensitizer, a crosslinking agent and a polymerizable compound. A volume phase hologram recording medium which comprises the styrylcoumarin compound, a crosslinking agent and a polymer comprising a carbazole.

12 Claims, 5 Drawing Sheets

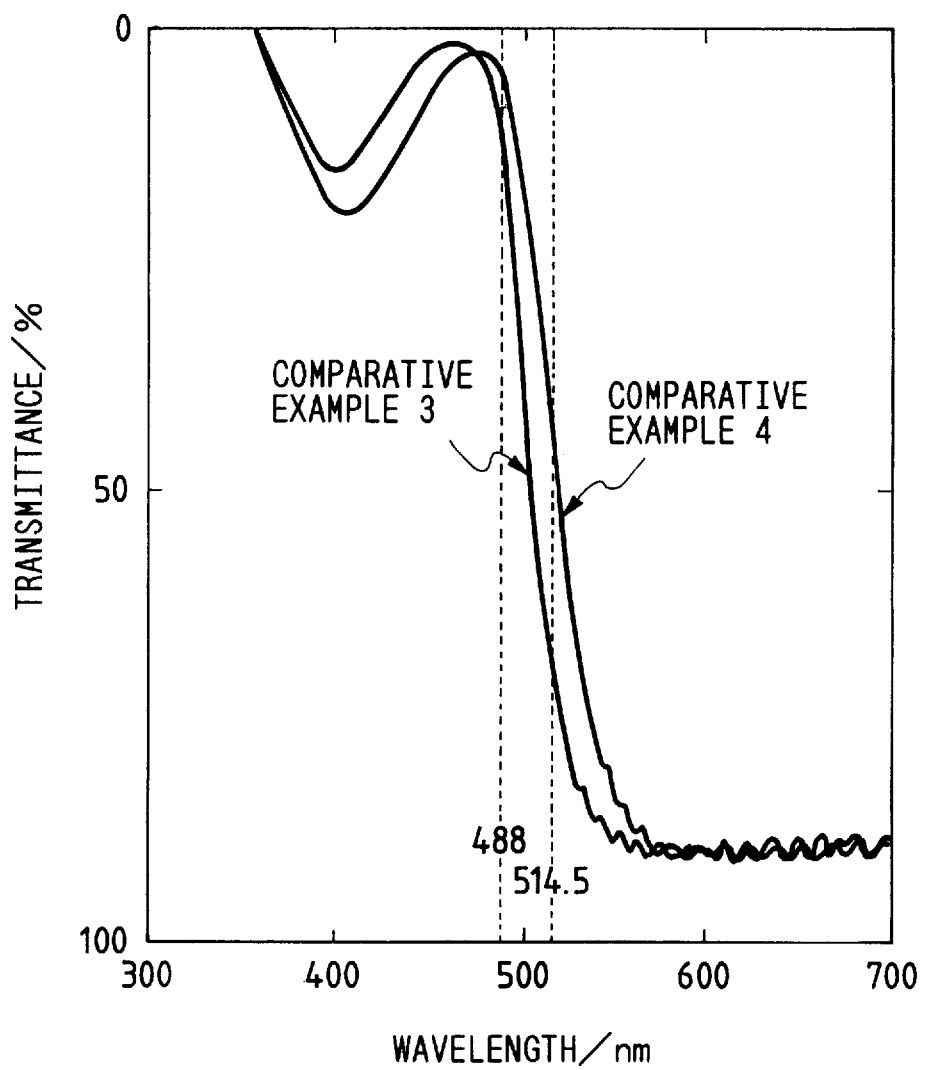

STYRYLCOUMARIN COMPOUND, PHOTOSENSITIVE RESIN COMPOSITION, AND HOLOGRAM RECORDING MEDIUM

This application is a continuation of application Ser. No. 08/625,303, filed Apr. 1, 1996, now abandoned; which, in turn, is a continuation of application Ser. No. 08/237,105 filed May 3, 1994 now abandoned.

BACKGROUND OF THE INVENTION

1. Field of the Invention

The present invention relates to a novel styrylcoumarin derivative, and more specifically, it relates to a photosensitizer comprising a styrylaminocoumarin derivative which functions as a photosensitizer (a sensitizing dye) for a polymerization initiator and/or a crosslinking agent, a photopolymerizable and/or photocrosslinkable photosensitive composition using the photosensitizer, and a hologram recording medium containing the photosensitive composition as a main component.

2. Related Background Art

With the development of triplet sensitizers and dye lasers, various novel coumarin compounds have been synthesized. Above all, ketocoumarins have absorption maximum ranging from 330 nm to 470 nm and so they have been developed as effective triplet sensitizers [Tetrahedron, 38, p. 1211 (1982)].

In consequence, nowadays, the coumarin compounds have been widely used as the photosensitizers for polymerization initiators such as diphenyliodonium salts, triazine, peroxides and halogen compounds. Above all, compounds represented by the formulae (1) to (3) are known as preferable photosensitizers in a photosensitive system using an argon laser at 488 nm.

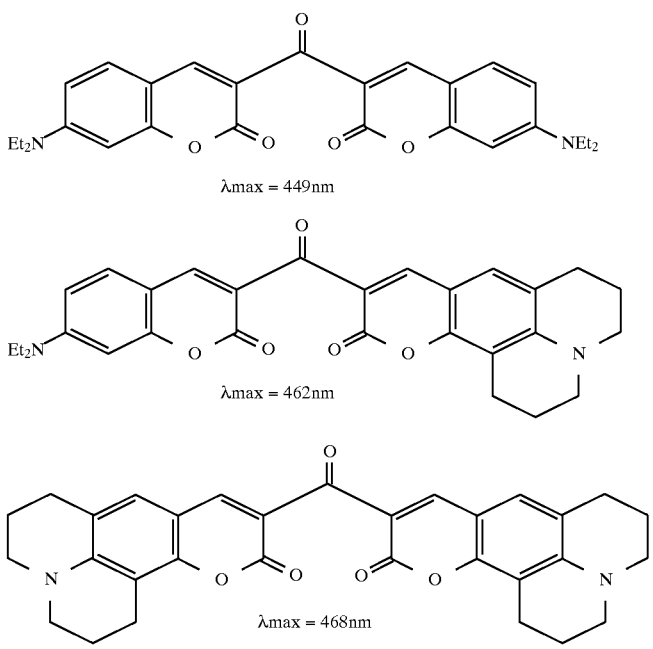

However, these dyes have absorption maximums in a wavelength region shorter than 488 nm, and a wavelength of 514.5 nm for the argon laser is their absorption edges. Therefore, it is necessary to enhance their sensitivity. In order to enhance the sensitivity of a photosensitive material, an absorbance of the photosensitive material is required to be increased, and as a conventional technique for increasing the absorbance, there has been only one method of increasing the amount of a dye.

In recent years, for the purpose of solving these problems, it has been suggested to use a styrylcoumarin compound represented by the following structural formula (4) as a photosensitizer (a sensitizing dye) [Polymer Engineering And Science, 23, p. 1022 (1983)]. However, the suggested photosensitizer is not sufficiently suitable for exposure at 514.5 nm by the argon laser.

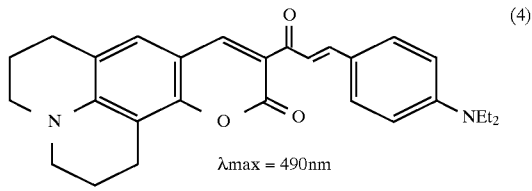

SUMMARY OF THE INVENTION

Thus, an object of the present invention is to provide a novel styrylcoumarin compound which can solve the problems of the above-mentioned conventional techniques and which can realize a high sensitivity at a wavelength of 488 nm of an argon laser and even at a wavelength of 514.5 nm or more.

Another object of the present invention is to provide an excellent photopolymerizable and/or photocrosslinkable photosensitive composition in which the styrylcoumarin compound is used as a sensitizer.

Still another object of the present invention is to provide a hologram recording medium in which the photosensitive composition is used as a main component.

The above-mentioned objects can be achieved by the following present inventions. That is, the first aspect of the present invention is directed to a styrylcoumarin compound selected from the group consisting of compounds each having a styryl group represented by the following structural formulae (a) to (d):

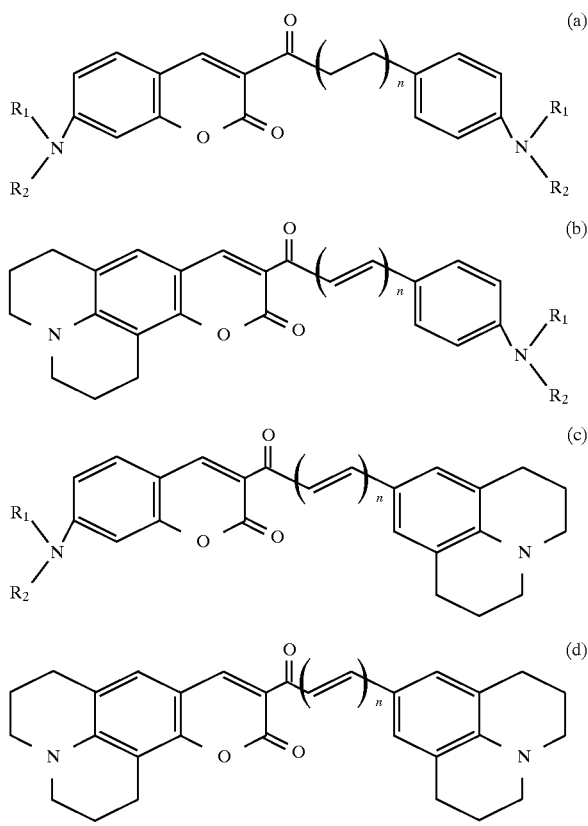

wherein n is an integer of 2 to 4, and each $R_1$ and $R_2$ is a proton or an alkyl group having 1 to 10 carbon atoms.

The second aspect of the present invention is directed to a photosensitive resin composition comprising the above-mentioned styrylcoumarin compound, a polymerization initiator or a crosslinking agent, and a polymerizable compound.

The third aspect of the present invention is directed to a volume phase hologram recording medium in which a polymer mainly comprising a carbazole is used as a crosslinkable compound.

BRIEF DESCRIPTION OF THE DRAWINGS

FIG. 6 is an absorption spectrum of dye in Comparative Examples 3 and 4.

DETAILED DESCRIPTION OF THE PREFERRED EMBODIMENTS

Figure 1:
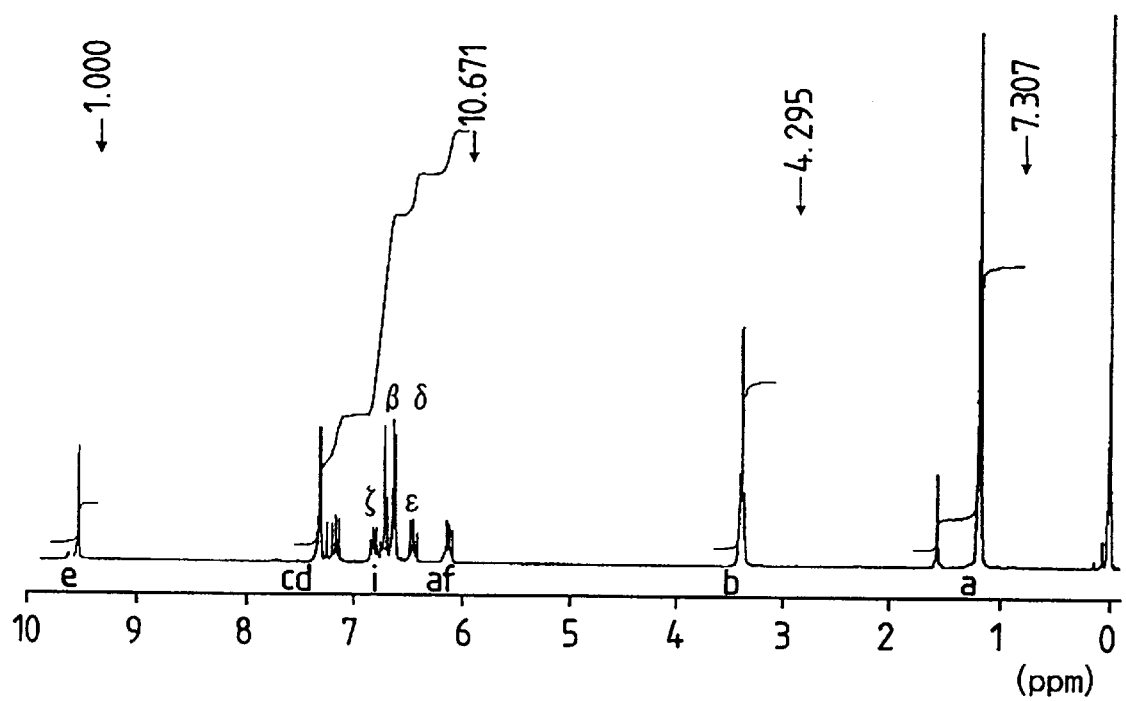
FIG. 1 is a spectrum of proton NMR.

The present inventors have intensively researched with the intention of solving the problems of the above-mentioned conventional techniques, and as a result, we have found that the absorption maximum of a styrylaminocoumarin compound can shift to longer wavelengths by increasing the number of double bonds in the styryl group of the styrylaminocoumarin compound and such a styrylaminocoumarin compound shows an excellent photosensitization. In consequence, the present invention has now been attained.

Usually, with regard to cyanine dye and the like, it has usually been known that the number of double bonds of each cyanine dye is increased in order to shift the absorption maximum of the cyanine dye to longer wavelengths, but with regard to coumarin compounds (coumarin dyes), such a technique has not been known so far. Furthermore, as the synthetic process of an aldehyde represented by the following formula having double bonds which is a precursor of the dye, in the case of the synthesis of a compound having no amino group, there are known various synthetic methods such as a Vilsmeier reaction and a Wittig reaction. However, in the case of the synthesis of a compound having the amino group, each of these reactions changes, and therefore a suitable selection of a synthetic route, some improvements of the synthetic procedure or the like are required.

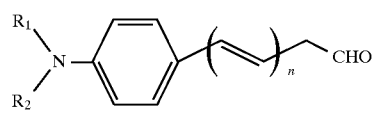

The present invention will be described in more detail in reference to preferable embodiments of the present invention.

The styrylcoumarin compound of the present invention is selected from the group consisting of compounds each having a styryl group represented by the following structural formulae (a) to (d):

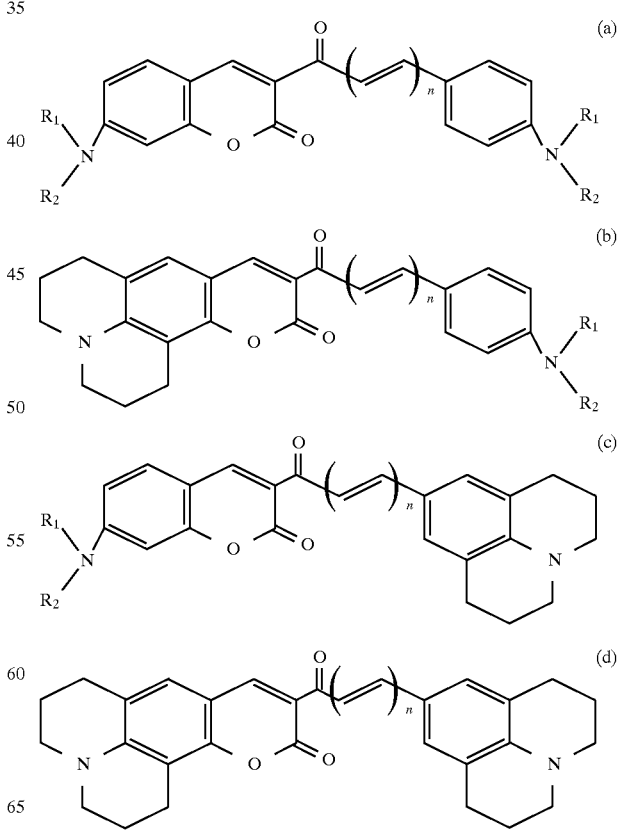

wherein n is an integer of 2 to 4, and each of $R_1$ and $R_2$ is a proton or an alkyl group having 1 to 10 carbon atoms.

These styrylcoumarin compounds can be synthesized in accordance with the following typical synthetic route:

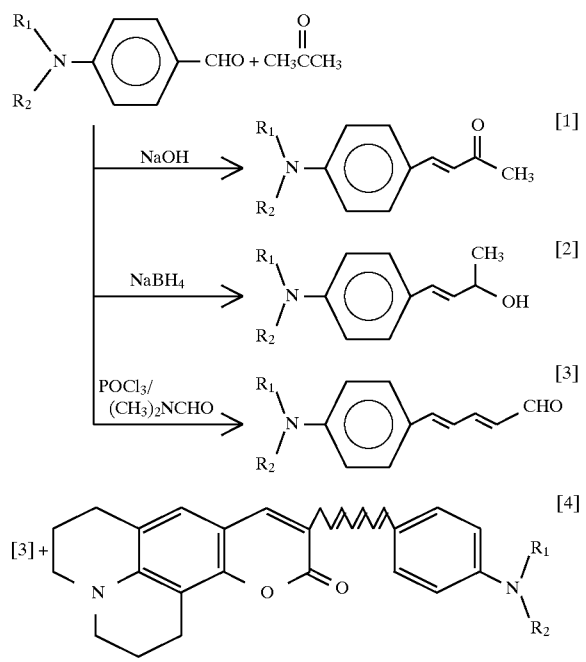

In case further increasing of the number of the double bonds is required, such a compound can be synthesized by repeatedly subjecting the above-mentioned reaction [1] or [2] to the compound [3].

Moreover, the aldehyde having one double bond can be synthesized by applying the process of making [3] from [2] to 1-(dialkylaminophenyl)-ethanol.

Also in case where an amino group takes a ring closure structure such as a julolidine group, a similar synthetic process can be employed. However, in this case, purification is necessary in each step so as to increase a reaction yield.

The styrylcoumarin compound of the present invention can be used as a photosensitizer (a sensitizing dye) for various polymerization initiators and/or crosslinking agents which are electron-accepting. Typical examples of these polymerization initiators and crosslinking agents include diarylhalonium derivatives, triazine derivatives, halogen compounds and peroxides which can be sensitized by conventional coumarin dyes.

The reaction mechanism of the sensitization by the styrylcoumarin compound can be considered to be due to the transfer of an electron from a triplet or singlet state which can be presumed in the usual coumarin compound, because the polymerization initiator and/or the crosslinking agent to be sensitized is electron-accepting.

Furthermore, the styrylcoumarin compound of the present invention permits the polymerization and/or the crosslinking of a compound having the double bond by triplet sensitization. For example, the styrylcoumarin compound can crosslink poly(vinyl cinnamate) together with an activation assistant.

The above-mentioned styrylcoumarin compound of the present invention can be used to prepare a photopolymerizable photosensitive resin composition of the present invention which comprises, as essential components, at least the styrylcoumarin compound, a polymerization initiator and a polymerizable compound such as a monomer.

Furthermore, the styrylcoumarin compound of the present invention can also be used to prepare a photocrosslinkable resin composition of the present invention which comprises, as essential components, at least the styrylcoumarin compound, a crosslinking agent and a polymerizable compound such as a polymer.

In these cases, an activation assistant, a polymer as a binder, and a plasticizer can be suitably added to the photosensitive resin composition in compliance with conditions.

Among the above-mentioned compositions, the photosensitive resin composition of a system comprising the styrylcoumarin compound, the crosslinking agent and a polymer mainly comprising a carbazole can be particularly preferably used as a volume phase hologram recording medium.

In this case, the concentration of the styrylcoumarin compound of the present invention can be adjusted in compliance with the film thickness of the volume phase hologram recording medium and the exposure wavelength in which the amount of the styrylcoumarin compound is determined in the range of $10^{-5}$ to $10^{-2}$ wt %, preferably $10^{-4}$ to $10^{-3}$ wt % based on the weight of a photosensitive solution.

Preferable usable examples of the polymerization initiator and/or the crosslinking agent which can be used in this case include diarylhalonium salt derivatives, halomethyl-S-triazine derivatives, halogen compounds and peroxides.

Diarylhalonium Salt Derivatives

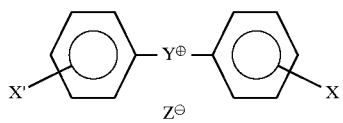

wherein

Y=I, Br or Cl,

Z=$PF_6$, $CF_3COO$, $ClO_4$, $SbF_6$, $BF_4$ or $AsF_6$,

X=an alkyl group or a halogen atom.

Halomethyl-S-triazine Derivatives

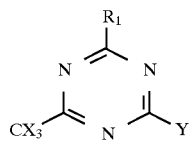

wherein

X=a halogen atom, preferably chlorine,

Y=$CX_3$, —$NH_2$, —NHR —OR or —SR (R=an alkyl group or an aryl group)

$R_1$=—$CX_3$, an alkyl group having 1 to 10 carbon atoms or an aryl group (the aryl group=Bz, BzCl or $BzCH_3O$)

Halogen Compounds $CI_4$, $CHI_3$ or $CBrCl_3$

Peroxides

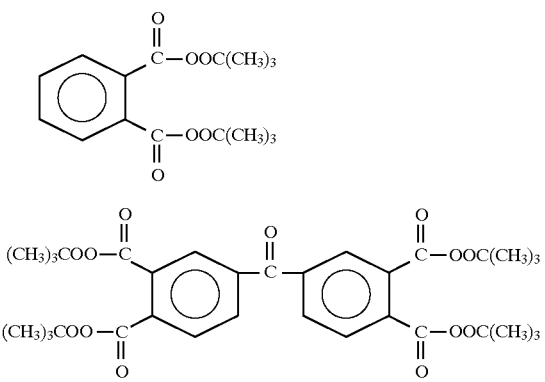

The polymerization initiator and/or the crosslinking agent is used preferably in an amount in the range of $10^{-4}$ to $10^{-1}$ wt %, more preferably $10^{-3}$ to $10^{-2}$ wt % based on the weight of the photosensitive solution.

The polymerizable compound which can be used in the photosensitive resin composition of the present invention is a compound containing at least one double bond, and examples of such a compound include monomers, prepolymers such as dimers and oligomers, and mixtures thereof.

Typical examples of the polymerizable compound include 1,5-pentandiol diacrylate, ethylene glycol diacrylate, 1,4-butanediol diacrylate, diethylene glycol diacrylate, hexamethylene glycol diacrylate, 1,3-propanediol diacrylate, decamethylene glycol diarylate, decamethylene glycol dimethacrylate, 1,4-cyclohexanediol diacrylate, 2,2-dimethylolpropane diacrylate, glycerol diacrylate, tripropylene glycol diacrylate, glycerol triacrylate, trimethylolpropane triacrylate, pentaerythritol triacrylate, polyoxy ethylate trimethylolpropane triacrylate and trimethacrylate, the same compounds as mentioned in U.S. Pat. No. 3,380,831, pentaerythritol tetraacrylate, triethylene glycol diacrylate, triethylene glycol dimethacrylate, polyoxypropyltrimethylolpropane triacrylate (462), ethylene glycol dimethacrylate, butylene glycol dimethacrylate, 1,3-propanediol dimethacrylate, 1,2,4-butanetriol trimethacrylate, 2,2,4-trimethyl-1,3-pentanediol dimethacrylate, pentaerythritol trimethacrylate, pentaerythritol tetramethacrylate, trimethylolpropane trimethacrylate, 1,5-pentanediol dimethacrylate and diallyl fumarate.

Moreover, diacrylates and dimethacrylates of bisphenol A and bisphenol A epoxy adducts are also useful as the polymerizable compounds, and typical examples thereof include di-(3-methacryloxy-2-hydroxypropyl) ether of bisphenol A, di-(2-methacryloxyethyl) ether of bisphenol A, di-(3-acryloxy-2-hydroxypropyl) ether of bisphenol A, di-(2-acryloxyethyl) ether of bisphenol A, ethoxylate bisphenol A diacrylate, di-(3-methacryloxy-2-hydroxypropyl) ether of tetrachloro-bisphenol A, di-(2-methacryloxyethyl) ether of tetrachloro-bisphenol A, di-(3-methacryloxy-2-hydroxypropyl) ether of tetrabromobisphenol A and di-(2-methacryloxyethyl) ether of tetrabromo-bisphenol A.

In addition, examples of the compounds useful as the polymerizable compounds include compounds each having an isocyanato group, for example, addition polymers of compounds such as 1,4-cyclohexyl diisocyanate, 1,3,5-cyclohexyl triisocyanate and 1,4-benzene diisocyanate, and 2-hydroxyethyl acrylate (methacrylate), 2-hydroxypropyl acrylate and the like.

Further examples of the polymerizable compounds include styrene, 2-chlorostyrene, phenyl acrylate, 2-phenylethyl acrylate, 2,2-di(p-hydroxyphenyl)propane diacrylate and methacrylate, 1,4-benzene diacrylate and methacrylate, 1,4-diisopropenylbenzene and 1,3,5-triisopropenylbenzene. However, the monomers which can be used in the present invention are not limited to the above-mentioned radical polymerizable monomers.

Further preferable examples of the radical polymerizable monomers which can be used in the present invention include isobornyl methacrylate, isobornyl acrylate, adamantyl acrylate, methacrylate, CR-39, and acrylates, methacrylates, diacrylates and dimethacrylates each having, on a side chain, dicyclopentadiene represented by the structural formula (X)

 (X)

for example, compounds having the following formulae:

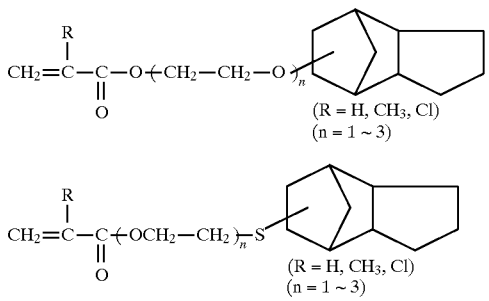

fenchyl methacrylate, L-menthyl methacrylate, dimethyladamantyl methacrylate, compounds represented by the following formula (I):

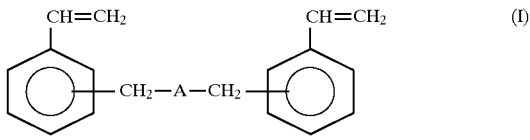 (I)

wherein A is

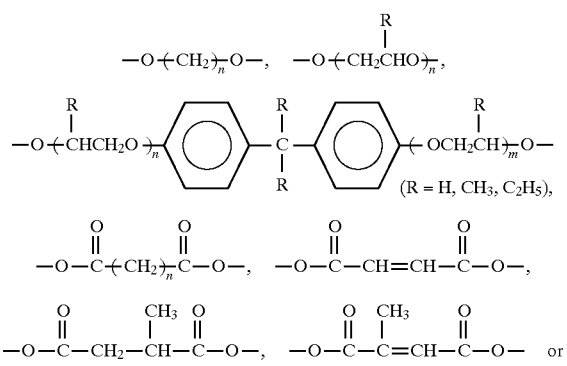 or

-continued

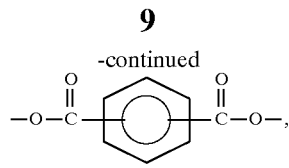

and compounds represented by the formulae:

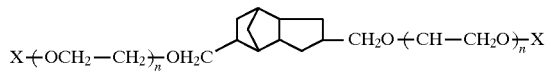

wherein X is

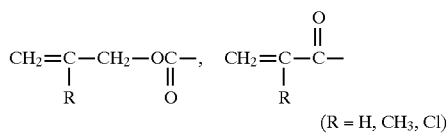

(R = H, CH₃, Cl)

In addition, the following vinyl ethers are also useful as the polymerizable monomers [J. V. Crivello et al., Journal of Polymer Science, Polymer Chemistry Ed., 21, p. 1785 (1983)]:

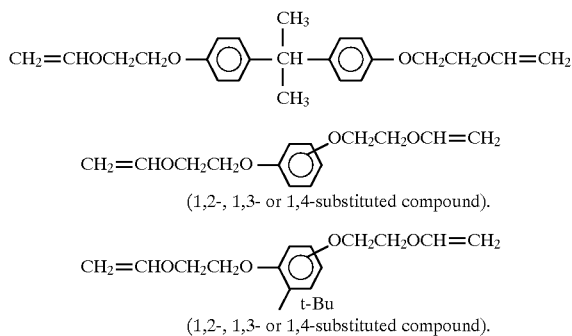

(1,2-, 1,3- or 1,4-substituted compound).

(1,2-, 1,3- or 1,4-substituted compound).

The following spiroorthoesters, spiroorthocarbonates and bicycloorthoesters are also useful as the polymerizable monomers. Particularly, these compounds scarcely contract at the time of the polymerization, and on this account, they are preferable to obtain a large refractive index modulation:

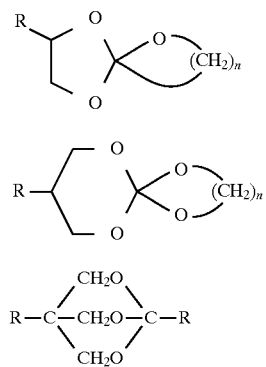

wherein R is an alkyl group or an alkoxy group, and n is an optional integer.

Each of these cationic polymerizable monomers is contained at a ratio of 10 to 60% by weight in the photosensitive resin composition of the present invention.

Furthermore, as the polymerizable monomers which can be used in the present invention, there can also be used compounds having a structure capable of performing cat-ionic and radical polymerization with an ethylenic unsaturated double bond in each molecule.

Examples of these compounds include vinyl monomers having a carbazole ring (capable of performing the cationic polymerization), for example, N-vinylcarbazole, 3-chlorovinylcarbazole and 3,6-dibromo-9-vinylcarbazole. In addition, a compound of the following structure having an epoxy ring and an ethylenic unsaturated double bond can also be used:

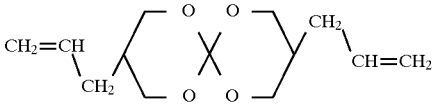

Typical examples of a polymer for use in the photopolymerizable or photocrosslinkable resin composition and the hologram recording medium using the photopolymerizable or photocrosslinkable resin composition of the present invention include polyvinylcarbazole, 3-chlorovinylcarbazole polymer, 3-bromovinylcarbazole polymer, 3-iodovinylcarbazole polymer, 3-methylvinylcarbazole polymer, 3-ethylvinylcarbazole polymer, chlorinated polyvinylcarbazole and brominated polyvinylcarbazole having an electron-donating aromatic ring, and polymers having an electron-donating side chain and comprising monomers represented by the following formulae:

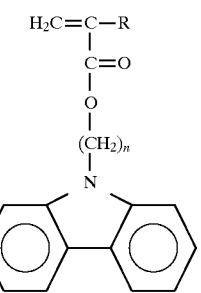

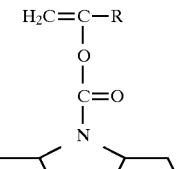

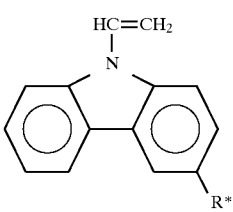

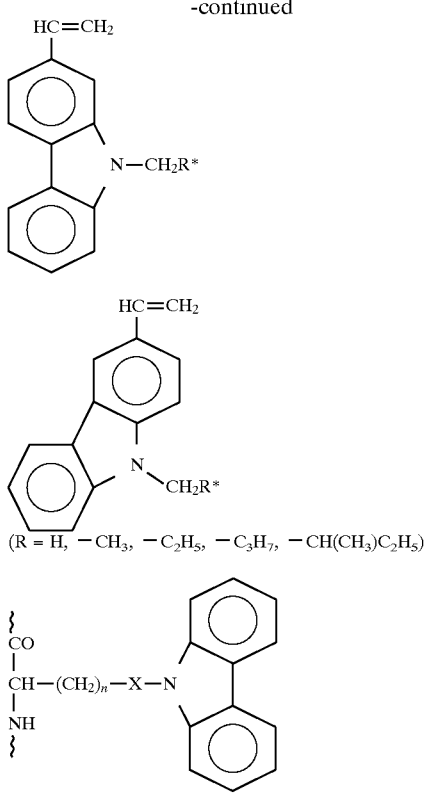

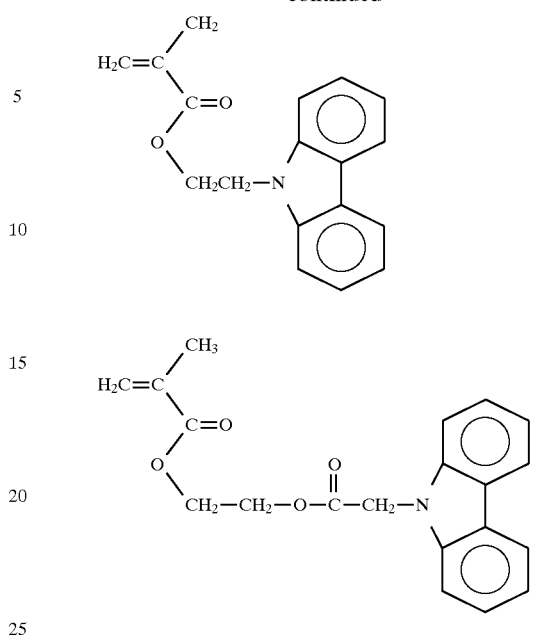

X and n in the above can be combined as follows, and four kinds of compounds are included:

n=1: —COOCH$_2$CH$_2$—
n=2: —COOCH$_2$CH$_2$—
n=4: —NHCO—
n=1: —SCH$_2$CH$_2$—

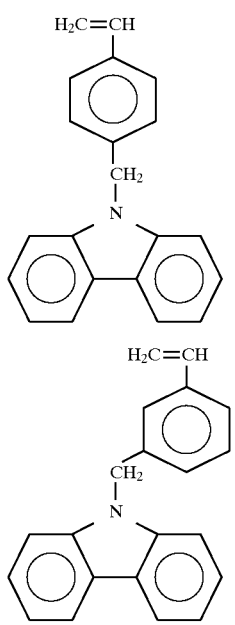

Other examples of the polymer containing, as a main constitutional unit, the monomer having the electron-donating side chain in the molecule includes polystyrenes having a halogen (—Cl, —Br or —I), p-amino, p-dimethylamino, p-methoxy and p-OH at the p-position, poly(N-vinylindole), poly(N-vinylpyrrole), poly(N-vinylphenothiazine), poly(isopropenylphenol) and poly[4-(N,N-diphenylamino)phenylmethyl methacrylate].

The above-mentioned vinylcarbazole polymer, if necessary, may be copolymerized with another monomer in order to control characteristics such as strength and flexibility of films obtained therefrom. Examples of the other monomer which can be used for such an application include vinyl monomers which can be copolymerized by a radical copolymerization, for example, olefins, vinyl esters such as vinyl acetate, acrylic acid, esters of methacrylic acid, styrene and styrene derivatives as well as the above-mentioned vinylcarbazoles.

The vinylcarbazole polymer, when used, can be blended with another polymer such as polystyrene, styrene-butadiene copolymer, styrene-hydrogenated butadiene copolymer, polycarbonates, polyacrylates, polyvinylbutyral or polyvinyl acetate, in an amount in a range in which a hologram image can be recorded. A ratio of the other polymer to be added can be selected so as to obtain the desired characteristics.

Reference has been just made to the essential constitutional components of the photosensitive resin composition of the present invention, but in compliance with purposes such as the increase in contrast, the improvement of heat stability and the improvement of film formation properties, a binder, a plasticizer, a stabilizer and the like can be suitably added to the photosensitive resin composition of the present invention.

As the binder, any compound can be used, so long as it is an organic linear polymer compatible with the above-mentioned essential components.

Examples of the binder include cellulose acetate lactate polymers; three-dimensional polymers of polymethyl methacrylate, acrylic polymers and interpolymers including a methyl methacrylate/methacrylic acid or methyl methacrylate/acrylic acid copolymer, and methyl methacrylate/acrylic acid or, $C_2$ to $C_4$ alkyl methacrylate/ acrylic acid or methacrylic acid; polyvinyl acetate; polyvinyl acetal; polyvinyl butyral and polyvinyl formal.

Examples of the plasticizer include triethylene glycol, triethylene glycol diacetate, triethylene glycol dipropionate, triethylene glycol dicaprilate, triethylene glycol dimethyl ether, triethylene glycol bis(2-ethyl hexanoate), tetraethylene glycol diheptanoate, poly(ethylene glycol), poly (ethylene glycol) methyl ether, isopropylnaphthalene, diisopropylnaphthalene, poly(propylene glycol)glyceryl tributylate, diethyl adipate, diethyl sebacate, tributyl phosphate, tris(2-ethylhexyl) phosphate, Buly 30 (trade name) $[C_{12}H_{25}(OCH_2CH_2)_4OH]$ and Buly 35 (trade name) $[C_{12}H_{25}(OH_2CH_2)_{20}OH]$.

Examples of the useful stabilizer include hydroquinone, phenidone, p-methoxyphenol, alkyl-substituted and aryl-substituted hydroquinone and quinones, t-butyl catechol, pyrogallol, copper resinate, naphthylamine, β-naphthol, cuprous chloride, 2,6-di-t-butyl-p-cresol, phenothiazine, pyridine, nitrobenzene, dinitrobenzene, p-toluquinone and chloranil.

Next, the present invention will be described with reference to examples and comparative examples.

The scope of the present invention should not be limited to these examples.

EXAMPLE 1

(A) Synthesis of 7-(p-diethylaminophenyl)-2,4,6-heptatriyunal

DMF (10.8 g) was cooled to 10° C. or less, and $POCl_3$ (10.8 g) was then added dropwise to DMF at 10° C. or less. Next, the mixture was cooled at 0° C. for 30 minutes.

Afterward, 6-(p-diethylaminophenyl)-2-hydroxy-3,5-hexadiene (14 g) and DMF (27 g) were added dropwise at 0° C. over 2 hours.

Next, reaction was carried out at 50° C. for 2 hours. After the reaction, the reaction product was cooled to 0° C., and sodium acetate (32 g) and water (77 ml) were added dropwise at 10° C. or less. After the addition, the solution was stirred at room temperature for 1 hour.

Afterward, 200 to 300 ml of water was added, and the solution was then washed with 500 ml of ether. The thus washed aqueous phase was made alkaline by adding a diluted sodium hydroxide solution at 10° C. or less. The precipitated crystals were filtered under reduced pressure, washed with water, extracted with $CHCl_3$, dried over $MgSO_4$, and then column-purified to synthesize 7-(p-diethylaminophenyl)-2,4,6-heptatriyunal.

In this case, yield was 18.5%.

The thus synthesized product was identified by proton NMR, and as a result, a spectrum shown in FIG. 1 and the results shown in Table 1 were obtained. In consequence, it was confirmed that the synthesized product was a compound having the following structure:

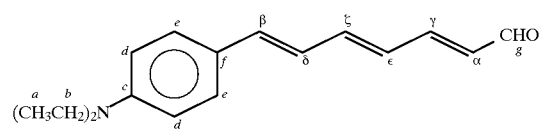

TABLE 1

| Chemical Shift δ Value (ppm) | Proton | Position | Coupling Constant |
| --- | --- | --- | --- |
| 1.18 | t | —$CH_3$ | a | 7Hz |
| 3.39 | q | —$CH_2$— | b | 7Hz |
| 6.13 | q | —CH | α | 15Hz, 8Hz |
| 6.45 | q | —CH | ε | 15Hz, 11Hz |
| 6.69 | q | —CH | δ | 15Hz, 10Hz |
| 6.74 | d | —CH | β | 14Hz |
| 6.63 | dd | —CH | d, e | 9Hz |
| 7.32 | | | | |
| 6.83 | q | —CH | ζ | 15Hz, 10Hz |
| 7.18 | q | —CH | γ | 15Hz, 12Hz |
| 9.55 | d | —CHO | g | 8Hz |

(2) Synthesis of Dye

A solution comprising $1.3 \times 10^{-3}$M of 7-(p-diethylaminophenyl)-2,4,6-heptatriyunal synthesized above, $1.3 \times 10^{-3}$M of a compound represented by the following formula, 0.142 g of piperidine and 3.4 ml of ethanol was heated on an oil bath at 75° C. for 2 hours. Next, the precipitated solid was collected by filtration, and then recrystallized from methanol and chloroform to obtain a styrylcoumarin dye.

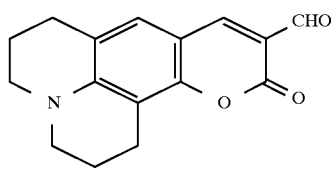

Figure 2:
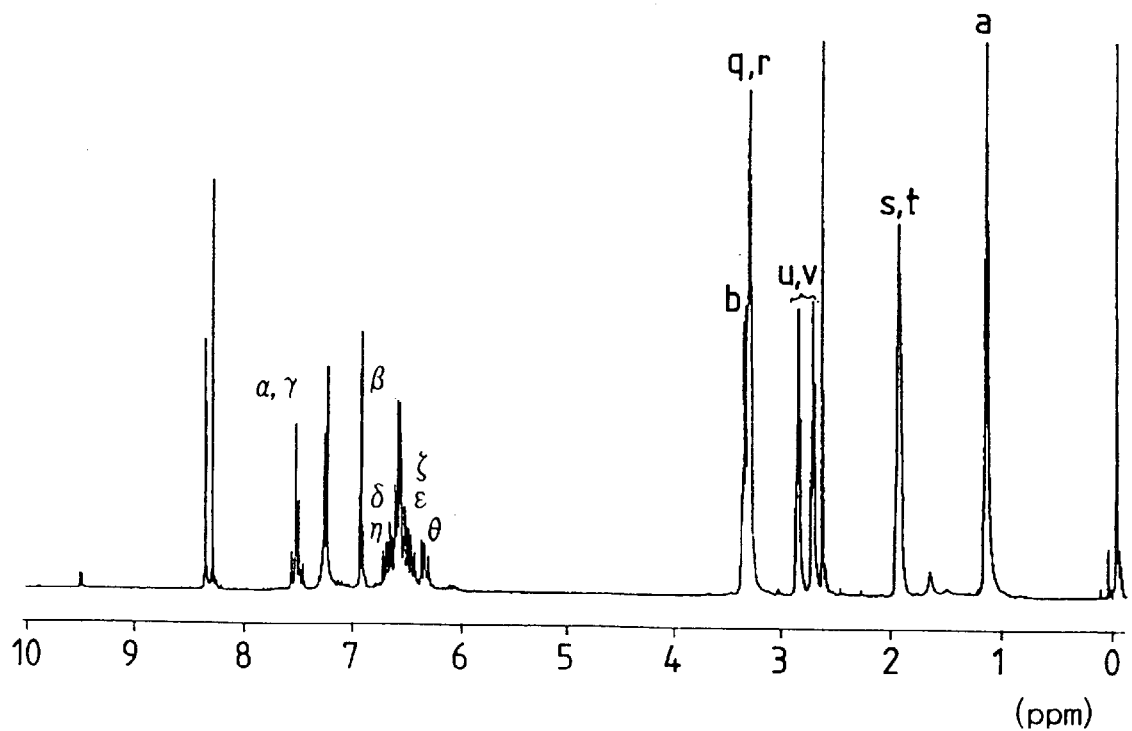
FIG. 2 is another spectrum of proton NMR.

The thus obtained dye was identified by proton NMR, and as a result, a spectrum shown in FIG. 2 and the results shown in Table 2 were obtained. In consequence, it was confirmed that the obtained dye was a compound having the following structure. In the measurement of NMR, chloroform ($CHCl_3$) was used as a solvent.

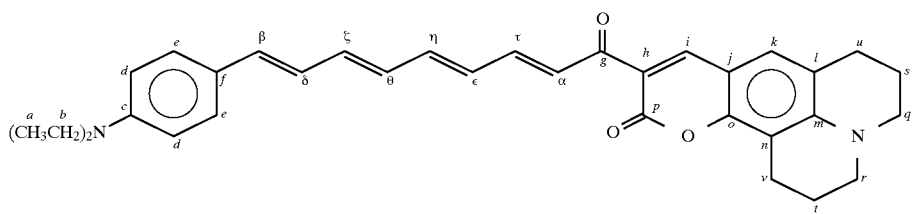

TABLE 2

| Chemical Shift δ Value (ppm) | | Proton | Position | Coupling Constant |
|---|---|---|---|---|
| 1.13 | t | —CH₃ | a | 7Hz |
| 1.92 | m | —CH₂— | s, t | |
| 2.71 | t | —CH₂— | u, v | 6, 4Hz |
| 2.85 | | | | |
| 3.29 | m | —CH₂— | q, r | |
| 3.33 | q | —CH₂— | b | 7, 3Hz |
| 6.37 | dd | —CH | ε | 15, 10Hz |
| 6.50 | dd | —CH | γ | 15, 11Hz |
| 6.52 | dd | —CH | ζ | 15, 11Hz |
| 6.58 | m | —CH | θ | |
| 6.68 | dd | —CH | η | 15, 11Hz |
| 6.73 | dd | —CH | δ | 15, 11Hz |
| 6.52 | d | —CH | β | 15Hz |
| 6.91 | s | —CH | k | |
| 6.57 | dd | —CH | d, e | 8, 8Hz |
| 7.24 | | | | |
| 7.55 | d | —CH | α | 3Hz |
| 8.28 | s | —CH | i | |

Figure 3:
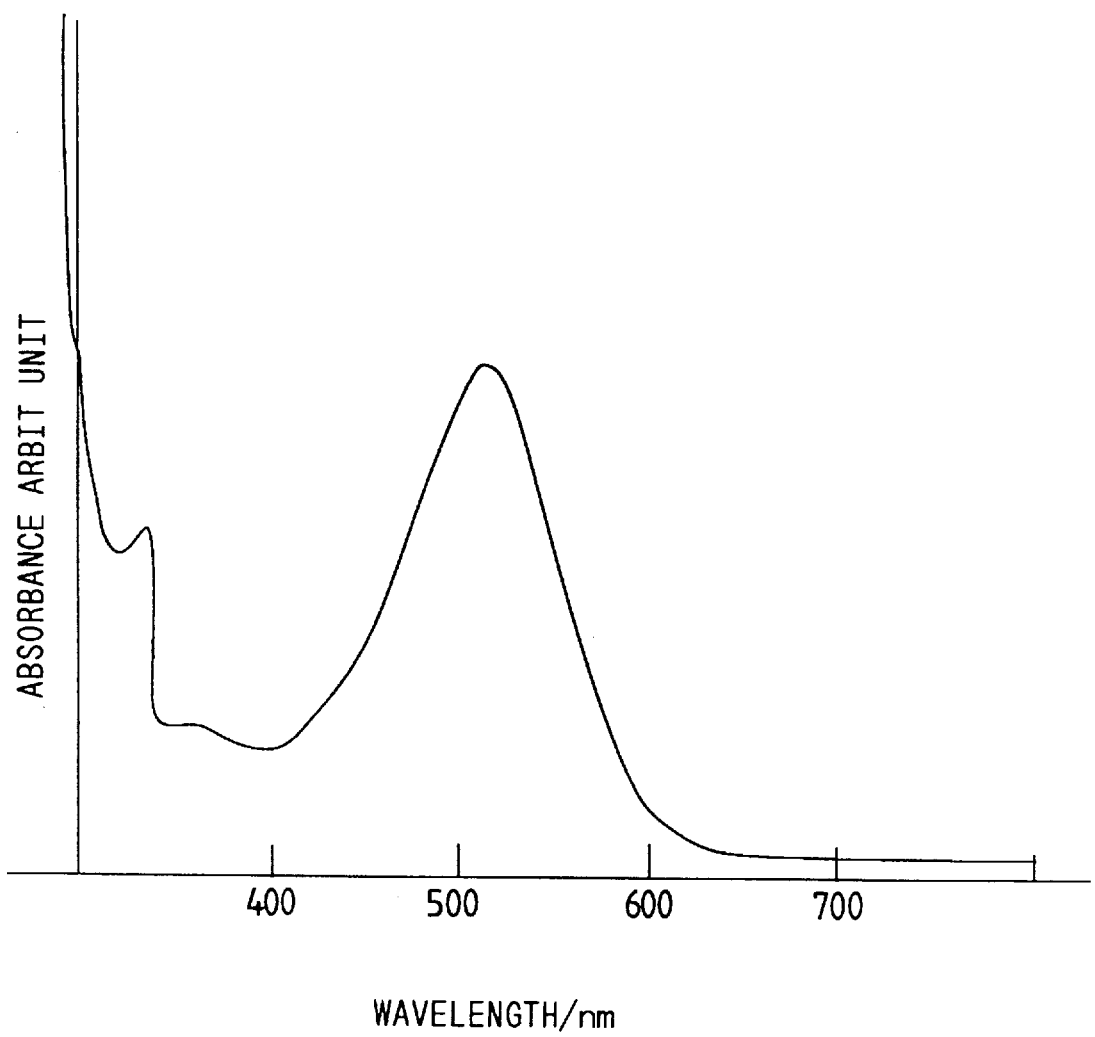
FIG. 3 is an absorption spectrum of the solution of a dye in Example 1.

The obtained compound had an absorption maximum at 515 nm in chloroform as shown in FIG. 3.

EXAMPLE 2

Following the same procedure as in Example 1, a dye with double bonds which is different from the compound of Example 1 in length of double bonds was synthesized.

The thus synthesized compound was identified by proton NMR, and the results are shown in Table 3.

TABLE 3

| Chemical Shift δ Value (ppm) | | Proton | Position | Bond Constant |
|---|---|---|---|---|
| 1.18 | t | —CH₃ | a | 6, 8Hz |
| 1.97 | m | —CH₂— | s, t | |
| 2.85 | t | —CH₂— | u, v | 6, 4Hz |
| 2.72 | | | | |
| 3.29 | q | —CH₂— | q, r | 5, 4Hz |
| 3.38 | q | —CH₂— | b | 7, 3Hz |
| 6.51 | d, d | —CH | ε | 14, 10Hz |
| 6.64 | d | —CH | β | 15Hz |
| 6.72 | d, d | —CH | δ | 15, 10Hz |
| 6.78 | d, d | —CH | ζ | 15, 10Hz |
| 6.61 | d, d | —CH | d, e | 9Hz |
| 7.29 | | | | |
| 6.98 | s | —CH | k | |
| 7.54 | m | —CH | γ | |
| 7.56 | d | —CH | α | 3Hz |
| 8.41 | s | —CH | i | |

EXAMPLE 3

Following the same procedure as in Example 1, a dye was synthesized.

The thus synthesized compound was identified by proton NMR, and the results are shown in Table 4.

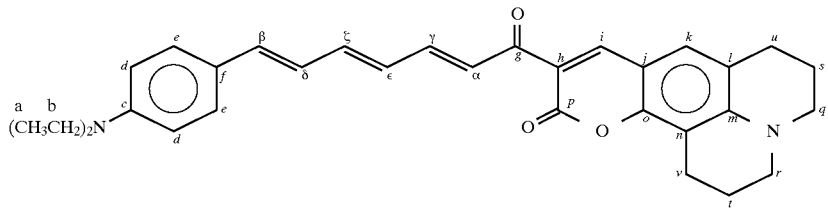

| Chemical Shift δ Value (ppm) | Proton | Position | Coupling Constant |
|---|---|---|---|
| 1.18 | t | —CH₃ | a | 7Hz |
| 1.98 | m | —CH₂— | s, t | |
| 2.76 | t | —CH₂— | u, v | 6Hz |
| 2.90 | | | | |
| 3.28 | q | —CH₂— | q, r | 5Hz |
| 3.39 | q | —CH₂— | b | 7Hz |
| 6.88 | d | —CH | β | 15Hz |
| 6.88 | m | —CH | δ | |
| 6.99 | s | —CH | k | |
| 7.37 | d, d | —CH | d, e | 8, 8Hz |
| 6.63 | | | | |
| 7.64 | d, d | —CH | γ | 15, 10Hz |
| 7.59 | d | —CH | α | 3Hz |
| 8.43 | s | —CH | i | |

TABLE 4

| Chemical Shift δ Value (ppm) | Proton | Position | Coupling Constant |
|---|---|---|---|
| 1.96 | m | —CH₂— | s, t, a | |
| 2.75 | m | —CH₂— | u, v, z | |
| 3.2 | m | —CH₂— | q, r, b | |
| 6.50 | d, d | —CH | ε | 15, 7Hz |
| 6.58 | d | —CH | β | 15Hz |
| 6.70 | d, d | —CH | δ | 11, 15Hz |
| 6.79 | d, d | —CH | ζ | 15, 11Hz |
| 6.98 | s | —CH | e | |
| 6.98 | d | —CH | k | |
| 7.55 | d | —CH | α | 3Hz |
| 7.56 | d, d | —CH | γ | 15, 11Hz |
| 8.41 | s | —CH | i | |

TABLE 5

EXAMPLE 4

The same procedure as in Example 1 was repeated except that 7-(p-diethylaminophenyl)-2,4,6-heptatriyunal which was a starting material in Example 1 was replaced with the following julolidine compound, to synthesize a dye.

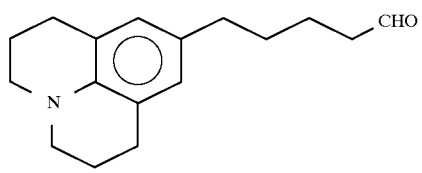

The thus synthesized compound was identified by proton NMR, and the results are shown in Table 5.

Figure 4:
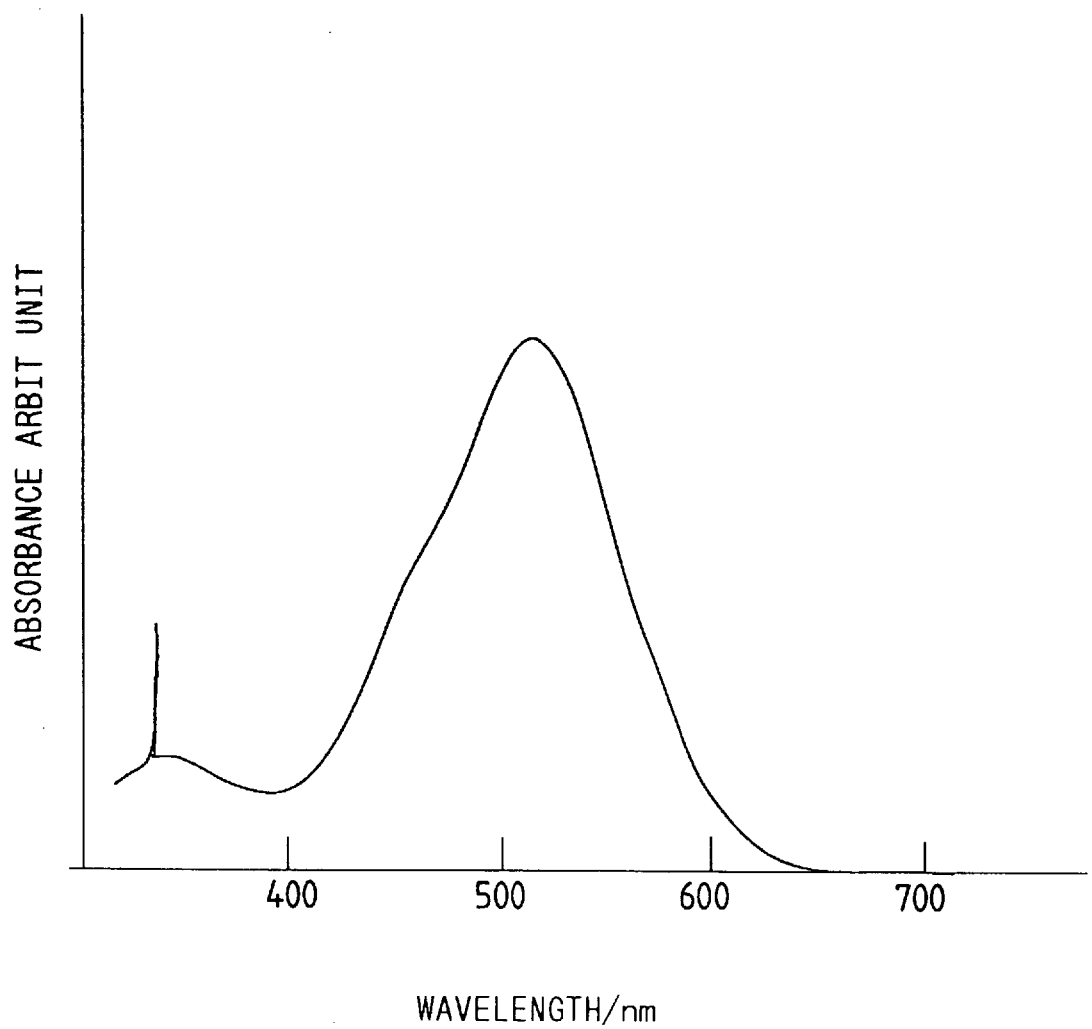
FIG. 4 is an absorption spectrum of the solution of a dye in Example 4.

The obtained compound had an absorption maximum at 515 nm in chloroform as shown in FIG. 4.

EXAMPLE 5

In 40 cc of chlorobenzene were dissolved 0.05 g of a styrylcoumarin dye synthesized in Example 1, 3 g of poly (p-chlorostyrene) and 0.1 g of di-t-butyldiphenylbromonium hexafluorophosphate to form a photosensitive solution.

A silicon wafer was spin-coated with this photosensitive solution so that its thickness might be 1 μm.

Next, lines and spaces of 1.5 μm were written on the thus obtained film by the use of light which was regulated to 515±5 nm with a xenon lamp and an interference filter.

Afterward, the film was heated at 130° C. for 1 minute, and then developed with dichloromethane. As a result, the obtained pattern could well reproduce the image of a mask, and the lines of 1.5 μm could be depicted.

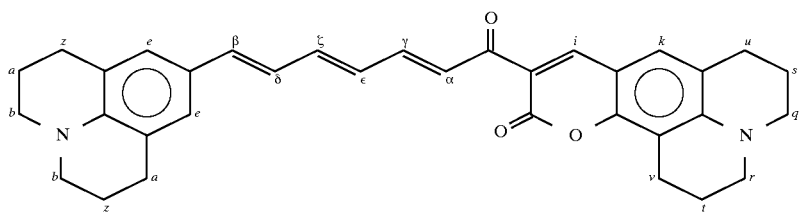

EXAMPLES 6 TO 9

Relief patterns were prepared by the use of the same procedure as in Example 5 under the following conditions, and as a result, lines of 1.5 μm could be depicted as in Example 5.

TABLE 6

| Example No. | Dye | Crosslinking Agent | Crosslikable Polymer | Exposure Wavelength |
|---|---|---|---|---|
| 6 | Example 1 | 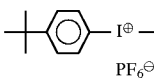 | Polyvinylcarbazole | 515 nm |
| 7 | Example 2 | 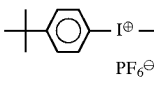 | Polyvinylcarbazole | 510 nm |
| 8 | Example 3 | 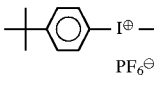 | Polyvinylcarbazole | 500 nm |
| 9 | Example 4 | 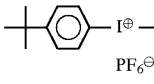 | Polyvinylcarbazole | 515 nm |

EXAMPLE 10

Components shown in Table 7 were dissolved in a mixed solution of chlorobenzene/dichloromethane=4/1, and a glass substrate was then coated with the mixture so that its thickness might be 3 μm, to obtain a hologram recording medium of the present invention.

TABLE 7

| Compound | wt % |
|---|---|
|  | 35 wt % |
| Dye of Example 2 | 1 wt % |
| Initiator $CHI_3$ | 2 wt % |
| Binder Polymer PMMA (Elvacite 2041 DuPont) | 35 wt % |

This recording medium was spin-coated with polyvinyl alcohol, and exposed to light, 515±5 nm, with a xenon lamp and an interference filter.

Afterward, the obtained film was heated at 80° C. for 5 minutes, and polyvinyl alcohol was then removed with an aqueous alcohol solution. Next, the film was washed with exlene, and at this time, the exposed areas were not removed, because they were crosslinked.

EXAMPLE 11

In 60 cc of chlorobenzene were dissolved 0.05 g of a styrylcoumarin dye synthesized in Example 1, 3 g of polyvinylcarbazole, 0.1 g of di-t-butyldiphenyliodonium hexafluorophosphate and 0.1 g of iodoform, thereby obtaining a photosensitive solution for a volume phase hologram recording medium of the present invention.

In a dark place, a glass substrate was coated with this solution by the use of a spinner so that its thickness might be 9 μm. The thus obtained recording medium was exposed at 50 mJ/cm² to light of 514.5 nm from $Ar^+$ laser in a reflective type hologram recording system.

The exposed recording medium was developed by the following procedure to obtain a reflective type volume phase hologram.

(1) 30° C.; xylene solution; 2 minutes.
(2) 30° C.; xylene:hexane=1:1 solution; 2 minutes.
(3) 30° C.; hexane; 2 minutes.

The thus obtained volume phase hologram had a diffraction efficiency of about 80%.

EXAMPLES 12 TO 14

Figure 5:
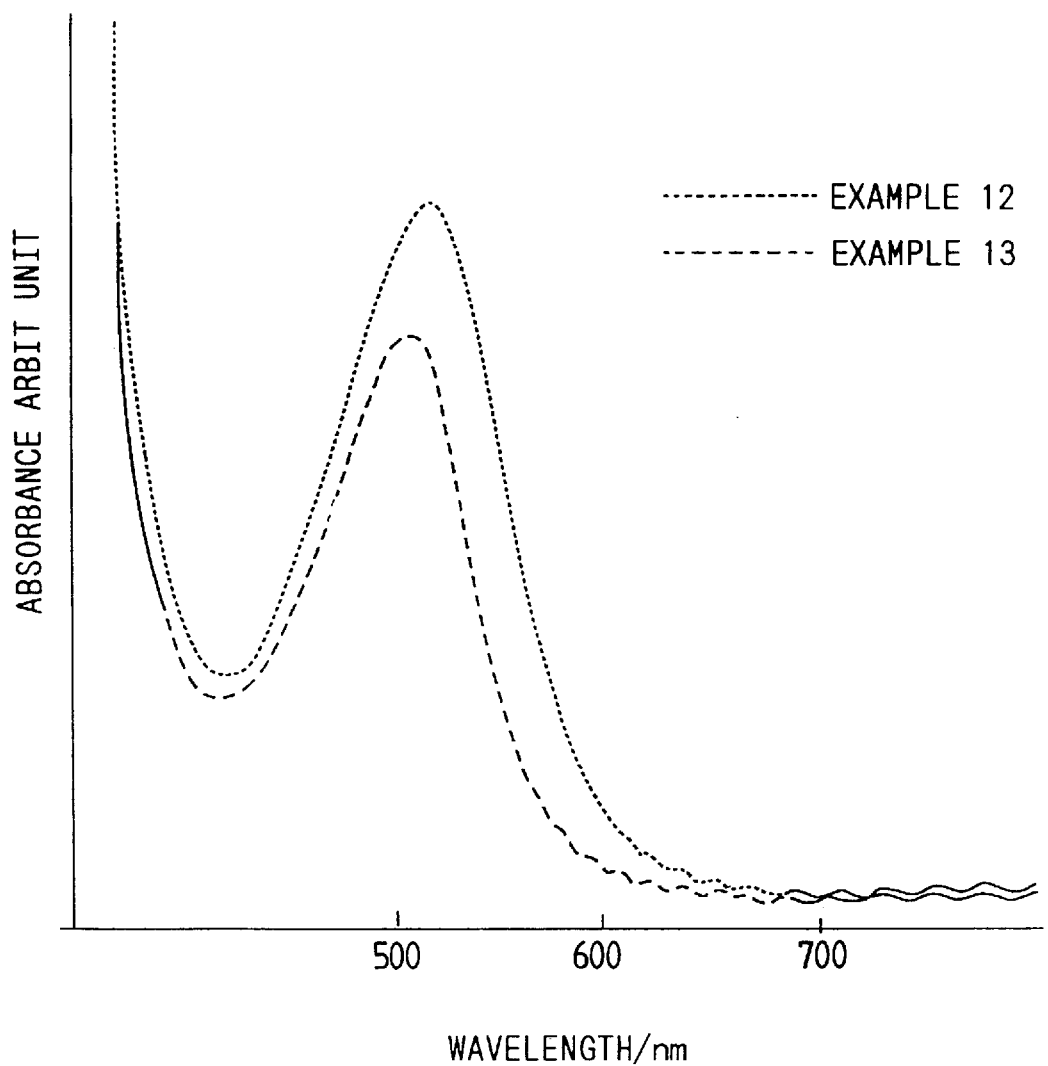
FIG. 5 is an absorption spectrum of a hologram recording medium.

The same procedure as in Example 11 was carried out except that conditions shown in Table 8 were used, to prepare a hologram. FIG. 5 shows absorption spectra obtained in Examples 12 and 13.

TABLE 8

| Example No. | Dye | Exposure wavelength | Conc. of Dye | Diffraction Efficiency |
|---|---|---|---|---|
| 12 | Example 2 | 514.5 nm | 0.05 g | About 70% |
| 13 | Example 3 | 514.5 nm | 0.07 g | About 70% |
| 14 | Example 4 | 514.5 nm | 0.05 g | About 75% |

COMPARATIVE EXAMPLES 1 AND 2

The same procedure as in Example 11 was carried out except that conditions shown in Table 9 were used, to prepare a hologram.

TABLE 9

| Comp. Ex. No. | Dye | Exposure Wavelength | Conc. of Dye | Diffraction Efficiency |
|---|---|---|---|---|
| 1 | 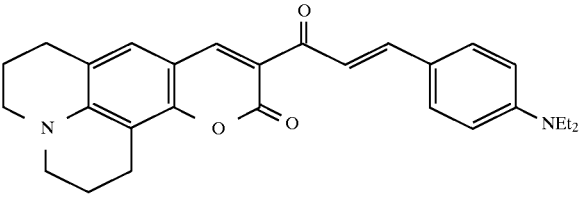 | 514.5 nm | 0.10 g | About 15% |
| 2 | | 488 nm | 0.05 g | About 70% |

COMPARATIVE EXAMPLES 3 AND 4

Hologram recording mediums were respectively prepared in the same manner in Example 12 except that another kind of dye shown in the following was used as a dye:

Dye used in Comparative Example 3

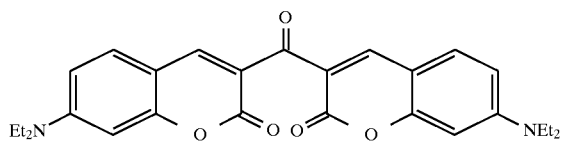

Dye used in Comparative Example 4

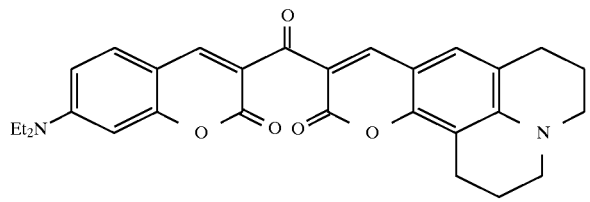

to obtain a hologram, respectively. The results of the absorption spectrum measurement in the obtained hologram recording mediums are shown in FIG. 6.

The obtained hologram in comparative Example 3 had little diffraction efficiency, and the obtained hologram in Comparative Example 4 has that of 5%.

As described above, a styrylcoumarin compound of the present invention has a high sensitivity at a wavelength of 488 nm of an argon laser and even at a wavelength of 514.5 nm or more and it shows excellent photopolymerizing and crosslinkable properties, because the styryl group in the compound has long conjugated double bonds and so its absorption maximum shifts to longer wavelengths.

In addition, by the utilization of this styrylcoumarin compound as a sensitizer, there can be provided an excellent photosensitive resin composition and a hologram recording medium in which the photosensitive resin composition is used as a main component.

What is claimed is:

1. A photocrosslinking composition which comprises a styrylcoumarin compound selected from the group consisting of coumarin compounds each having a styryl group represented by the following structural formulae (b) to (d)

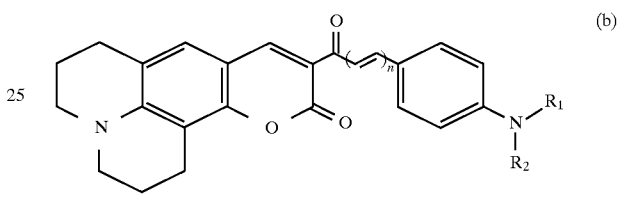 (b)

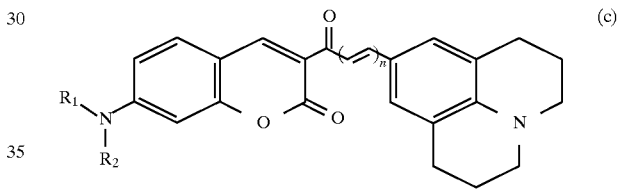 (c)

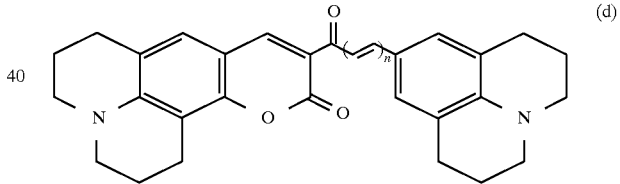 (d)

wherein n is 4 and each of $R_1$ and $R_2$ is a proton or an alkyl group having 1 to 10 carbon atoms as a photosensitizer, a crosslinking agent and a crosslinkable compound.

2. The photocrosslinking composition according to claim 1 wherein the crosslinking agent is electron-accepting.

3. The photocrosslinking composition according to claim 2, wherein the crosslinking agent is selected from the group consisting of diarylhalonium salts, halomethyl-S-triazines, halo-substituted methane and peroxides.

4. The photocrosslinking composition according to claim 1, wherein the styrylcoumarin is

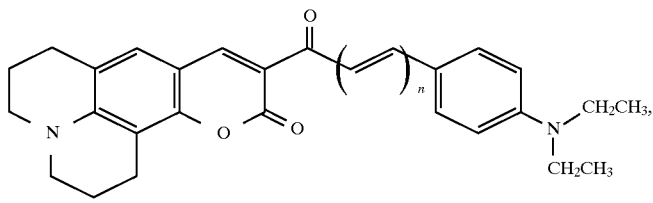

wherein n is 4

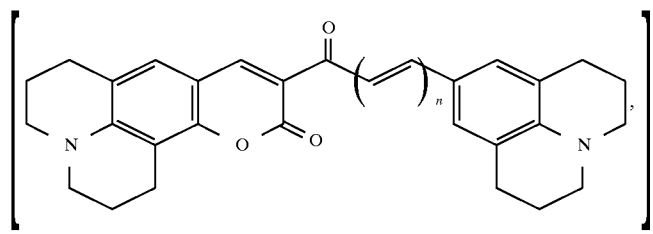

5. A volume phase hologram recording medium which comprises a styrylcoumarin compound selected from the group consisting of coumarin compounds each having a styryl group represented by the following structural formulae (b) to (d)

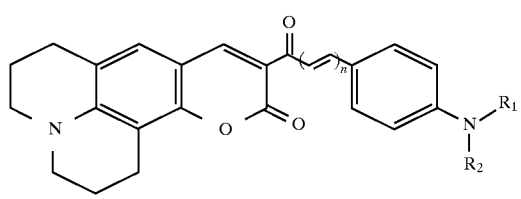
(b)

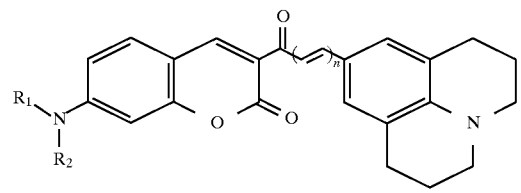
(c)

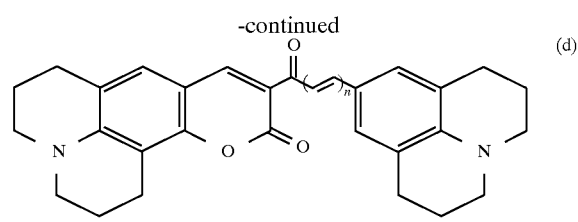
(d)

wherein n is 4 and each of $R_1$ and $R_2$ is a proton or an alkyl group having 1 to 10 carbon atoms, a crosslinking agent and a polymer comprising a carbazole.

6. The volume phase hologram recording medium according to claim 5 wherein the crosslinking agent is electron-accepting.

7. The volume phase hologram recording medium according to claim 5, wherein the crosslinking agent is selected from the group consisting of diarylhalonium salts, halomethyl-S-triazines, halo-substituted methane and peroxides.

8. The volume phase hologram recording medium according to claim 5, wherein the styrylcoumarin is

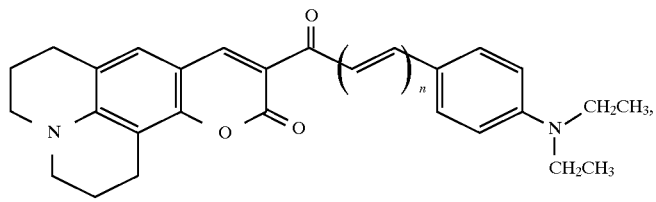

wherein n is 4

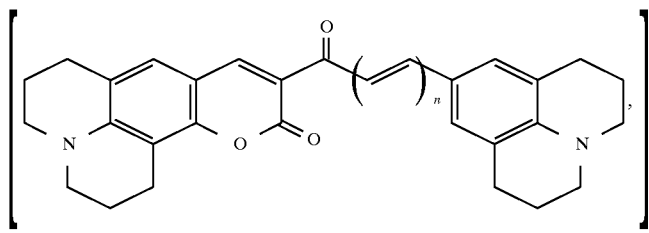

9. A photopolymerizable composition which comprises: (i) a styrylcoumarin photosensitizer compound selected from the group consisting of (b), (c) and (d) as follows:

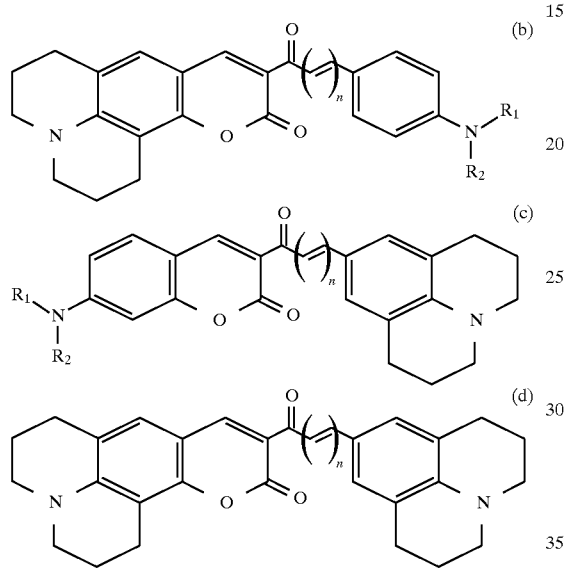

wherein n is 4 and each of $R_1$ and $R_2$ is a hydrogen atom or an alkyl group having 1 to 10 carbon atoms, (ii) a polymerization initiator and (iii) a polymerizable compound.

10. The photopolymerizable composition according to claim 9, wherein the polymerization initiator is electron-accepting.

11. The photopolymerizable composition according to claim 10, wherein the polymerization initiator is selected from the group consisting of diarylhalonium salts, halomethyl-S-triazines, halo-substituted methane and peroxides.

12. The photopolymerizable composition according to claim 9, wherein the styrylcoumarin photosensitizer compound is

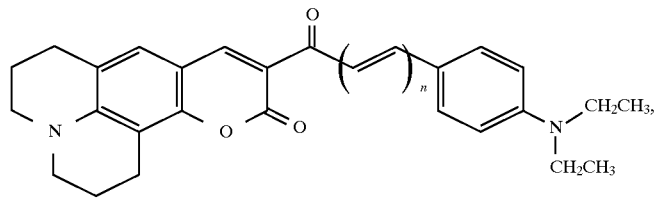

* * * * *

UNITED STATES PATENT AND TRADEMARK OFFICE
CERTIFICATE OF CORRECTION

PATENT NO. : 5,879,837
DATED : March 9, 1999
INVENTOR(S) : YOKO YOSHINAGA ET AL.

It is certified that error appears in the above-identified patent and that said Letters Patent is hereby corrected as shown below:

ON COVER PAGE AT [56] FOREIGN PATENT DOCUMENTS

"1-259702" should read --2-279702--.

ON COVER PAGE AT [56] OTHER PUBLICATIONS

"Cyanie" should read --Cyanine--;
"Experimetns in physical" should read --Experiments in Physical--.

COLUMN 5

Lines 24-29 " 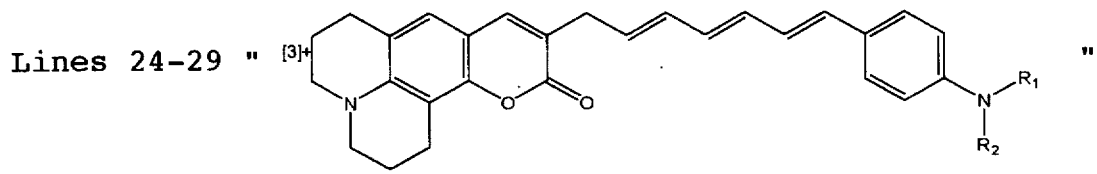 "

should read

UNITED STATES PATENT AND TRADEMARK OFFICE
CERTIFICATE OF CORRECTION

PATENT NO. : 5,879,837

DATED : March 9, 1999

INVENTOR(S) : YOKO YOSHINAGA ET AL.

Page 2 of 2

It is certified that error appears in the above-identified patent and that said Letters Patent is hereby corrected as shown below:

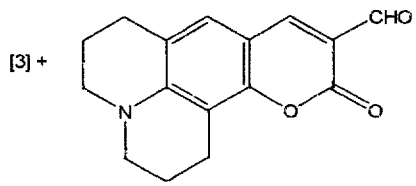

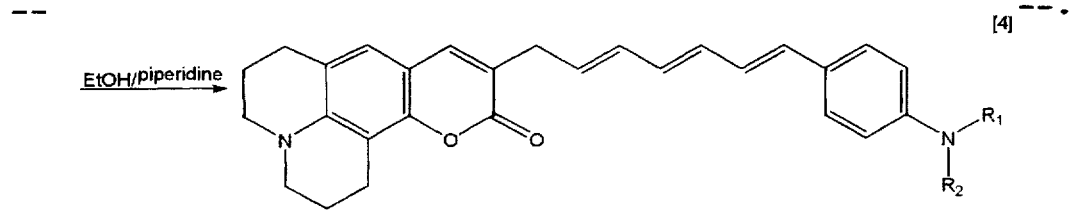

COLUMN 17

Lines 2-6 "  " should be deleted;

Signed and Sealed this

Twenty-second Day of February, 2000

Attest:

Q. TODD DICKINSON

Attesting Officer

Commissioner of Patents and Trademarks